(12) United States Patent
Kim

(10) Patent No.: US 6,327,720 B1
(45) Date of Patent: Dec. 11, 2001

(54) SAUNA MADE WITH ILLITE SURFACES

(76) Inventor: Il M. Kim, 212 S. Arnaz Dr. #6, Beverly Hills, CA (US) 90211

( * ) Notice: Subject to any disclaimer, the term of this patent is extended or adjusted under 35 U.S.C. 154(b) by 0 days.

(21) Appl. No.: 09/431,622

(22) Filed: Nov. 2, 1999

(51) Int. Cl.[7] ............................................... A61H 33/06
(52) U.S. Cl. ............................................................ 4/524
(58) Field of Search ................................................ 4/524

(56) References Cited

U.S. PATENT DOCUMENTS 4,956,030 * 9/1990 Baskin ............................... 156/61

FOREIGN PATENT DOCUMENTS

4141167 * 5/1992 (JP) ............................................. 4/524
5269178 * 10/1993 (JP) ............................................. 4/524

* cited by examiner

*Primary Examiner*—Charles E. Phillips
(74) *Attorney, Agent, or Firm*—John K. Park; Park & Sutton LLP

(57) ABSTRACT

A sauna made with illite surfaces is disclosed. The sauna comprises an internal enclosure member forming an internal cavity, an external enclosure member, and a means for heating the internal cavity. The internal enclosure member further comprises a bottom portion, a plurality of side portions and a ceiling portion. The internal enclosure member is attached to the external enclosure member, and the bottom portion, the side portions, and the ceiling portion of the internal member are respectively composed of about 10 to 90 percent illite by mass.

9 Claims, 1 Drawing Sheet

SAUNA MADE WITH ILLITE SURFACES

BACKGROUND OF THE INVENTION

This invention relates to a sauna chamber. More specifically, the present invention relates to an improved sauna made with illite surfaces, wherein each wall within a sauna chamber including a bottom portion thereof is formed of an illite composite material for thereby promoting conspicuous therapeutic effects together with deodorization effect.

A generally known illite refers to a group of clay minerals formed by weathering or hydrothermal alteration of other aluminium-rich minerals, and it is also known that illite occurs intermixed with kaoline and other clay minerals. Whereas, illite powder denotes natural radioactive clay particles that radiate a healthful quantity of infrared radiation.

Illite is also known as Bio-Light Stone or Sang Gwang Suk (Korean for Bio-Light Stone), as the illite powder radiates faint glow, and it can be naturally extracted from a clay deposit in form of powder, or rock that can be finely ground into a powder form. The main ingredients for illite powder are believed to be $SiO_2$, $Al_2O_3$, $K_2O$, $FeO$, $FeO_2$. The best illite powder for this invention comes from Republic of Korea, from the mines of the mining town of San-Ik-Rhee, the township of Young-Dong-Gun, the province of Choong-Chung-Book-Do.

Also, illite has been used for various industrial or residential purposes. For example, illite is a crucial element in sewage treatment because it has a certain antibacterial effects. Illite further generates strong negative ions that neutralize positive ions incurring bad odor.

The inventor found that the synergetic combination of illite and sauna significantly enhances therapeutic effects expected by most sauna users. Therefore, it is an object of the present invention to provide a sauna made with illite surfaces which is capable of deodorizing and pasteurizing the atmosphere within the sauna.

Another object of the present invention is to generate a healing or therapeutic effect for sauna users by taking advantage of an illite characteristic, wherein illite radiates far infrared radiations that are known to generate numerous positive effects on human body.

SUMMARY OF THE INVENTION

To achieve the aforementioned objects and other objects, a sauna according to the present invention comprises an internal enclosure member, an external enclosure member and a means for heating an internal cavity formed by the internal enclosure member. Here, the heating means may be one selected from a heated rock, an electrical heater and other commonly known sauna heating devices.

The internal enclosure member has a bottom portion, side portions and a ceiling portion, wherein the internal enclosure member is attached to the external enclosure member. The bottom portion, the side portions, and the ceiling portion of the internal member may be respectively composed of about 10 to 90 percent illite by mass.

According to an improvement of the present invention, the bottom portion of the internal enclosure member may be composed of about 50 to 90 percent illite by mass. Also, the side portions and the ceiling are respectively composed of about 20 to 50 percent illite by mass. Preferably, the respective bottom portion, side portions and the ceiling portion may be also composed of about 20 to 50 percent illite by mass.

For a better performance, the internal enclosure member may be formed unitary with the external enclosure member. Selectively, a plurality of illite particles are densely populated within the internal enclosure member in a constant and regular illite concentration. Further, the illite concentration in the internal enclosure member may become incrementally greater toward the cavity.

The advantages of the present invention are numerous. First, the illite composite sauna wall deodorizes hazardous gas and/or bad smell in the air, thereby realizing a clear atmosphere within the sauna. Second, illite pasteurizes the atmosphere by intensively radiating negative ions and subsequently provides an antibacterial effect, thereby securing a healthy and refreshed air to the full satisfaction of the sauna users. Third, the illite mineral radiates far infrared radiations of 3 to 25 $\mu$m in wave length for thereby generating a therapeutic effect on the sauna users.

Although the present invention is briefly summarized, the fuller understanding of the invention can be obtained by the following drawings, the detailed description and appended claims.

BRIEF DESCRIPTION OF THE DRAWING

The present invention will be better understood with reference to the accompanying drawing, wherein.

DETAILED DESCRIPTION OF THE PREFERRED EMBODIMENTS

Figure 1:
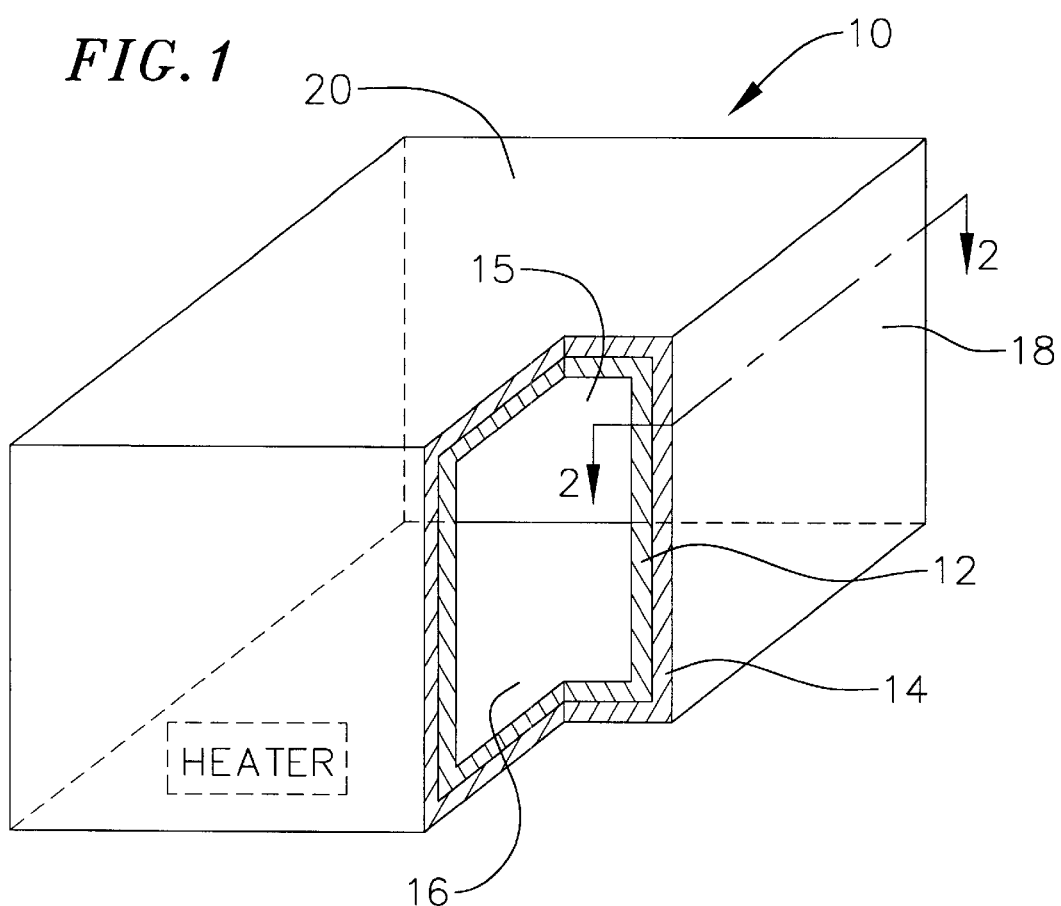
FIG. 1 is a partially sectional view illustrating a sauna according to the present invention.

The present invention is directed to a sauna made with illite surfaces. As shown in FIG. 1, a sauna 10 according to the present invention comprises an internal enclosure member 12, an external enclosure member 14, and a means (not shown) for heating an internal cavity 15 formed by the internal enclosure member 12.

Here, the sauna 10 denotes a heat emitting bath chamber enclosed by sauna walls or the internal enclosure member 12, and the heating means (not shown) may be one selected from a heated rock, an electrical heater and other commonly known sauna heating devices. The internal enclosure member 12 of the sauna 10 has a bottom portion 16, side portions 18 and a ceiling 20 portion, and the internal enclosure member 12 is attached to the external enclosure member 14. Selectively, the internal enclosure member 12 may be integrally formed unitary with the external enclosure member 14.

Also, a plurality of planar wall partitions may be employed to form the internal enclosure member 14 so as to facilitate wall construction for the sauna 10.

According to an embodiment of the present invention, the bottom portion 16, the side portions 18, and the ceiling portion 20 of the internal enclosure member 12 are respectively composed of about 10 to 90 percent illite by mass.

In another embodiment, the bottom portion 16 of the internal enclosure member 12 is composed of about 50 to 90 percent illite by mass.

Also, in still another embodiment, the side portions 18 and the ceiling 20 may be respectively composed of about 20 to 50 percent illite by mass. For a better performance, the respective bottom portion 16, side portions 18 and ceiling 20 may be composed of about 20 to 50 percent illite by mass.

Figure 2:
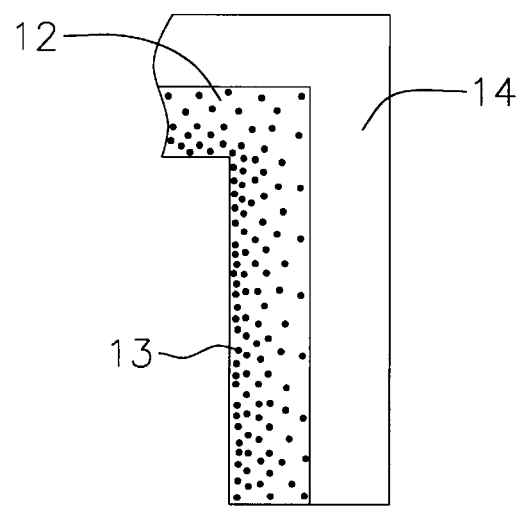
FIG. 2 is a cross-sectional view taken along line 2—2 in FIG. 1.

As further shown in FIG. 2, a plurality of illite particles 13 are densely populated within the internal enclosure member 12. That is, an illite concentration in the internal enclosure member 12 is constantly and evenly maintained. Selectively, the illite concentration in the internal enclosure member 12 may become incrementally greater toward the cavity 15.

Illite is known as an environmentally beneficial mineral material that radiates far infrared radiations, and its application reaches various industrial fields, including sewage filtration, deodorization and pasteurization. The concept of the present invention is to combine sauna and illite using their respective therapeutic and characteristic benefits.

To maximize a sauna effect, the present invention recommends each internal sauna wall including bottom and ceiling to be formed of a admixture of illite and any of such conventional sauna wall materials as painting, plaster and other commonly known wall materials.

The advantages of the present invention are numerous. First, the illite composite sauna wall deodorizes hazardous gas and/or bad smell in the air, thereby realizing a clear atmosphere within the sauna.

Second, illite pasteurizes the atmosphere by intensively radiating negative ions and subsequent antibacterial effect, thereby securing a healthy and refreshed air to the full satisfaction of the sauna users.

Third, the illite mineral radiates far infrared radiations of 3 to 25 $\mu$m in wave length for thereby generating a therapeutic effect on the sauna users.

Furthermore, because illite's beneficial qualities are permanent, the sauna according to this invention can maintain its enhanced quality for a longer duration, and negative ions released from illite powder have unusually refreshing sense of cleanness and purity.

Although the present invention has been described in considerable detail with reference to certain preferred versions thereof, other versions are possible by converting the aforementioned construction. Therefore, the scope of the invention shall not be limited by the specification specified above and the appended claims.

What is claimed is:

1. A sauna comprising an internal enclosure member forming an internal cavity, an external enclosure member, and a means for heating the internal cavity, wherein the internal enclosure member further comprises a bottom portion, a plurality of side portions and a ceiling portion, wherein the internal enclosure member is attached to the external enclosure member, and wherein the bottom portion, the side portions, and the ceiling portion of the internal member are respectively composed of about 10 to 90 percent illite by mass.

2. The sauna of claim 1, wherein the bottom portion of the internal enclosure member is composed of about 50 to 90 percent illite by mass.

3. The sauna of claim 1, wherein the side portions and the ceiling of the internal enclosure member are respectively composed of about 20 to 50 percent illite by mass.

4. The sauna of claim 1, wherein the bottom portion, the side portions and the ceiling portion of the internal enclosure member are respectively composed of about 20 to 50 percent illite by mass.

5. The sauna of claim 2, wherein the internal enclosure member is integrally formed unitary with the external enclosure member.

6. The sauna of claim 3, wherein the internal enclosure member is integrally formed unitary with the external enclosure member.

7. The sauna of claim 4, wherein the internal enclosure member is integrally formed unitary with the external enclosure member.

8. The sauna of claim 1, wherein an illite concentration in the internal enclosure member is constantly and evenly maintained.

9. The sauna of claim 1, wherein an illite concentration in the internal enclosure member becomes incrementally greater toward the cavity.

\* \* \* \* \*